United States Patent [19]

Kleemann et al.

[11] Patent Number: 5,631,293

[45] Date of Patent: May 20, 1997

[54] PREPARATION OF AMINO ACID-SUBSTITUTED BENZOYLGUANIDINES AS DIAGNOSTIC AGENTS

[75] Inventors: Heinz-Werner Kleemann, Bischofsheim; Hans-Jochen Lang, Hofheim; Jan-Robert Schwark, Frankfurt; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 525,204

[22] Filed: Sep. 8, 1995

[30] Foreign Application Priority Data

Sep. 9, 1994 [DE] Germany .................... 44 32 101.5

[51] Int. Cl.[6] .................... A61K 31/165; A61K 31/27; C07C 271/14; C07C 279/22

[52] U.S. Cl. .................... 514/563; 514/478; 514/486; 514/634; 514/542; 560/27; 562/439; 562/465; 562/469

[58] Field of Search ............. 560/27; 562/439, 562/465, 469; 514/478, 486, 563, 634, 542

[56] References Cited

U.S. PATENT DOCUMENTS

| | | |
|---|---|---|
| 3,780,027 | 12/1973 | Craqoe et al. . |
| 5,091,394 | 2/1992 | Englert et al. .................... 514/3.31 |
| 5,364,868 | 11/1994 | Englert et al. .................... 514/331 |

FOREIGN PATENT DOCUMENTS

| | | |
|---|---|---|
| 2099445 | 1/1994 | Canada . |
| 0556672 | 8/1993 | European Pat. Off. . |
| 0556674A1 | 8/1993 | European Pat. Off. . |
| 0589336 | 3/1994 | European Pat. Off. . |
| 0627413 | 12/1994 | European Pat. Off. . |
| 3502629 | 7/1986 | Germany . |

OTHER PUBLICATIONS

Derwent Abstract of CA 2,099,445.
Derwent Abstract of DE 3,502,629.
Derwent Abstract of EP 589336.
Derwent Abstract of EP 627413.

*Primary Examiner*—Jose G. Dees
*Assistant Examiner*—Lily Ledynh
*Attorney, Agent, or Firm*—Finnegan, Henderson, Farabow, Garrett & Dunner, L.L.P.

[57] ABSTRACT

Amino acid-substituted benzoylguanidines, a process for their preparation, their use as a medicament or diagnostic agent and a medicament containing them Benzoylguanidines of the formula I

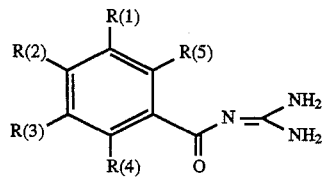

in which the radicals R(1) to R(5) have the meanings given in the description, are described. They are prepared by reacting a compound of the formula II

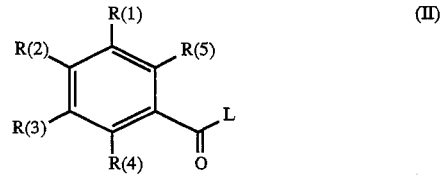

in which R(1) to R(5) and L have the meanings given in the description, with guanidine. The compound I is suitable for the preparation of cardiovascular medicaments.

9 Claims, No Drawings

PREPARATION OF AMINO ACID-SUBSTITUTED BENZOYLGUANIDINES AS DIAGNOSTIC AGENTS

The invention relates to benzoylguanidines of the formula I

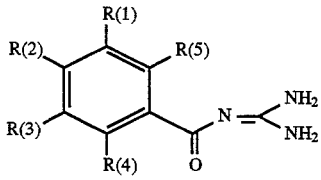

in which:

one of the three substituents R(1), R(2) and R(3) is
—Y—[4-[(CH$_2$)$_k$—CHR(7)—(C=O)R(8)]phenyl],
—Y—[3-[(CH$_2$)$_k$—CHR(7)—(C=O)R(8)]phenyl] or
—Y—[2-[(CH$_2$)$_k$—CHR(7)—(C=O)R(8)]phenyl], in which the phenyl is in each case unsubstituted or substituted by 1–2 substituents from the group consisting of F, Cl, —CF$_3$, methyl, hydroxyl, methoxy and —NR(37)R(38);

R(37) and R(38) independently of one another are hydrogen or —CH$_3$;

Y is a bond, oxygen, —S— or —NR(9);

R(9) is hydrogen or —(C$_1$-C$_4$)-alkyl;

R(7) is —OR(10) or —NR(10)R(11);

R(10) and R(11) independently of one another are hydrogen, —(C$_1$-C$_8$)-alkyl, —(C$_1$-C$_8$)-alkanoyl, —(C$_1$-C$_8$)-alkoxycarbonyl, benzyl, benzyloxycarbonyl;

or

R(10) is trityl;

R(8) is —OR(12) or —NR(12)R(13);

R(12) and R(13) independently of one another are hydrogen, —(C$_1$-C$_8$)-alkyl or benzyl;

k is zero, 1, 2, 3 or 4;

and the other particular radicals R(1), R(2) and R(3) independently of one another are —(C$_1$-C$_8$)-alkyl, —(C$_2$-C$_8$)-alkenyl or —(CH$_2$)$_m$R(14);

m is zero, 1 or 2;

R(14) is —(C$_3$-C$_8$)-cycloalkyl or phenyl, which is unsubstituted or substituted by 1–3 substituents chosen from the group consisting of F, Cl, —CF$_3$, methyl, methoxy and —NR(15)R(16);

R(15) and R(16) are hydrogen or —CH$_3$;

or the other particular radicals R(1), R(2) and R(3) independently of one another are R(18)R(19)N—(C=Y') NH—SO$_2$—;

Y' is oxygen, —S— or —N—R(20);

R(18) and R(19) independently of one another are hydrogen, —(C$_1$-C$_8$)-alkyl, —(C$_3$-C$_6$)-alkenyl or —(CH$_2$)$_t$—R(21);

t is zero, 1, 2, 3 or 4;

R(21) is —(C$_5$-C$_7$)-cycloalkyl or phenyl, which is unsubstituted or substituted by 1–3 substituents chosen from the group consisting of F, Cl, —CF$_3$, methoxy and —(C$_1$-C$_4$)-alkyl;

or

R(18) and R(19) together are 4 or 5 methylene groups, one CH$_2$ group of which can be replaced by oxygen, —S—, —NH—, —N—CH$_3$ or —N-benzyl;

R(20) is as defined for R(18) or amidine;

or the other particular radicals R(1), R(2) and R(3) independently of one another are hydrogen, F, Cl, Br, I, —C≡N, X—(CH$_2$)$_p$—(C$_q$F$_{2q+1}$), R(22)—SO$_u$—, R(23)R(24)N—CO—, R(25)—CO— or R(26)R(27) N—SO$_2$—, in which the perfluoroalkyl group is straight-chain or branched;

X is a bond, oxygen, —S— or —NR(28);

u is zero, 1 or 2;

p is zero, 1 or 2;

q is 1, 2, 3, 4, 5 or 6;

R(22), R(23), R(25) and R(26) independently of one another are —(C$_1$-C$_8$)-alkyl, —(C$_3$-C$_6$)-alkenyl, —(CH$_2$)$_n$—R(29) or —CF$_3$;

n is zero, 1, 2, 3 or 4;

R(28) is hydrogen or —(C$_1$-C$_3$)-alkyl;

R(29) is —(C$_3$-C$_7$)-cycloalkyl or phenyl, which is unsubstituted or substituted by 1–3 substituents chosen from the group consisting of F, Cl, —CF$_3$, methyl, methoxy and —NR(30)R(31);

R(30) and R(31) are hydrogen or —(C$_1$-C$_4$)-alkyl;

or

R(23), R(25) and R(26) are hydrogen;

R(24) and R(27) independently of one another are hydrogen or —(C$_1$-C$_4$)-alkyl;

or

R(23) and R(24) and R(26) and R(27), together are 4 or 5 methylene groups, one CH$_2$ group of which can be replaced by oxygen, —S—, —NH—, —N—CH$_3$ or —N-benzyl;

or the other particular radicals R(1), R(2) and R(3) independently of one another are —OR(35) or —NR(35)R(36);

R(35) and R(36) independently of one another are hydrogen or —(C$_1$-C$_6$)-alkyl;

or

R(35) and R(36) together are 4–7 methylene groups, one CH$_2$ group of which can be replaced by oxygen, —S—, —NH—, —N—CH$_3$ or —N-benzyl;

R(4) and R(5) independently of one another are hydrogen, —(C$_1$-C$_4$)-alkyl, F, Cl, —OR(32), —NR(33)R(34) or —C$_r$F$_{2r+1}$;

R(32), R(33) and R(34) independently of one another are hydrogen or —(C$_1$-C$_3$)-alkyl;

r is 1, 2, 3 or 4;

and pharmaceutically tolerated salts thereof.

Preferred compounds of the formula I are those in which:

R(1) is —(C$_1$-C$_4$)-alkyl, —(C$_2$-C$_4$)-alkenyl or —(CH$_2$)$_m$ R(14);

m is zero, 1 or 2;

R(14) is —(C$_5$-C$_6$)-cycloalkyl or phenyl, which is unsubstituted or substituted by 1–2 substituents chosen from the group consisting of F, Cl, —CF$_3$, methyl, methoxy and —NR(15) R(16);

R(15) and R(16) independently of one another are hydrogen or —CH$_3$;

or

R(1) is R(18)R(19)N—(C=Y')—NH—SO$_2$—;

Y' is oxygen, —S— or —N—R(20);

R(18) and R(19) independently of one another are hydrogen, —(C$_1$-C$_4$)-alkyl, —(C$_3$-C$_4$)-alkenyl or —(CH$_2$)$_t$—R(21);

t is zero, 1 or 2;

R(21) is —($C_5$–$C_6$)-cycloalkyl or phenyl, which is unsubstituted or substituted by 1–2 substituents chosen from the group consisting of F, Cl, —$CF_3$, methoxy and methyl;

or

R(18) and R(19) together are 4 or 5 methylene groups, one $CH_2$ group of which can be replaced by oxygen, —S—, —NH—, —N—$CH_3$ or —N-benzyl;

R(20) is as defined for R(18) or amidine;

or

R(1) is hydrogen, F, Cl, Br, I, —C≡N, R(22)—$SO_2$—, R(23)R(24)N—CO—, R(25)—CO— or R(26)R(27)N—$SO_2$—;

R(22), R(23), R(25) and R(26) independently of one another are —($C_1$–$C_4$)-alkyl, —($C_3$–$C_4$)-alkenyl, —($CH_2$)$_n$—R(29) or —$CF_3$;

n is zero, 1 or 2;

R(29) is —($C_5$–$C_6$)-cycloalkyl or phenyl, which is unsubstituted or substituted by 1–2 substituents chosen from the group consisting of F, Cl, —$CF_3$, methyl, methoxy and —NR(30) R(31);

R(30) and R(31) independently of one another are hydrogen or methyl;

or

R(23), R(25) and R(26) are hydrogen;

R(24) and R(27) independently of one another are hydrogen or methyl;

or

R(23) and (R24) and R(26) and R(27), together are 4 or 5 methylene groups, one $CH_2$ group of which can be replaced by oxygen, —S—, —NH—, —N—$CH_3$ or —N-benzyl;

or

R(1) is —OR(35) or —NR(35)R(36);

R(35) and R(36) independently of one another are hydrogen or —($C_1$–$C_4$)-alkyl;

or

R(35) and R(36) together are 4–5 methylene groups, one $CH_2$ group of which can be replaced by oxygen, —S—, —NH—, —N—$CH_3$ or —N-benzyl;

one of the substituents R(2) or R(3) is —Y—[4-[($CH_2$)$_k$—CHR(7)—(C═O)R(8)]phenyl], —Y—[3-[($CH_2$)$_k$—CHR(7)—(C═O)R(8)]phenyl] or —Y—[2-[($CH_2$)$_k$—CHR(7)—(C═O)R(8)]phenyl], in which the phenyl is in each case unsubstituted or substituted by 1–2 substituents from the group consisting of F, Cl, —$CF_3$, methyl, hydroxyl, methoxy or —NR(37)R(38);

R(37) and R(38) independently of one another are hydrogen or —$CH_3$;

Y is a bond, oxygen, —S— or —NR(9);

R(9) is hydrogen or methyl;

R(7) is —OR(10) or —NR(10)R(11);

R(10) and R(11) independently of one another are hydrogen, —($C_1$–$C_5$)-alkyl, —($C_1$–$C_5$)-alkanoyl, —($C_1$–$C_4$)-alkoxycarbonyl, benzyl or benzyloxycarbonyl;

or

R(10) is trityl;

R(8) is —OR(12) or —NR(12)R(13);

R(12) and R(13) independently of one another are hydrogen, —($C_1$–$C_4$)-alkyl or benzyl;

k is zero, 1 or 2;

and the other particular substituent R(2) or R(3) is —($C_1$–$C_4$)-alkyl, hydrogen, F, Cl, Br or I;

R(4) and R(5) independently of one another are hydrogen, methyl, F, Cl, —OR(32), —NR(33)R(34) or —$CF_3$;

R(32), R(33) and R(34) independently of one another are hydrogen or methyl;

and pharmaceutically tolerated salts thereof.

Particularly preferred compounds of the formula I are those in which:

R(1) is —($C_1$–$C_4$)-alkyl, —($C_2$–$C_4$)-alkenyl or —($CH_2$)$_m$R(14);

m is zero, 1 or 2;

R(14) is —($C_5$–$C_6$)-cycloalkyl or phenyl, which is unsubstituted or substituted by 1–2 substituents chosen from the group consisting of F, Cl, —$CF_3$, methyl, methoxy and —NR(15)R(16);

R(15) and R(16) independently of one another are hydrogen or —$CH_3$;

or

R(1) is hydrogen, F, Cl, Br, I, —C≡N, R(22)—$SO_2$—, R(23)R(24)N—CO—, R(25)—CO— or R(26)R(27)N—$SO_2$—;

R(22), R(23), R(25) and R(26) independently of one another are methyl or —$CF_3$, or R(23), R(25) and R(26) are hydrogen;

R(24) and R(27) independently of one another are hydrogen or methyl;

or

R(1) is —OR(35) or —NR(35)R(36);

R(35) and R(36) independently of one another are hydrogen or —($C_1$–$C_4$)-alkyl;

or

R(35) and R(36) together are 4–5 methylene groups, one $CH_2$ group of which can be replaced by oxygen, —S—, —NH—, —N—$CH_3$ or —N-benzyl;

one of the substituents R(2) and R(3) is —Y—[4-[($CH_2$)$_k$—CHR(7)—(C═O)R(8)]phenyl], —Y—[3-[($CH_2$)$_k$—CHR(7)—(C═O)R(8)]phenyl] or —Y—[2-[($CH_2$)$_k$—CHR(7)—(C═O)R(8)]phenyl], in which the phenyl is in each case unsubstituted or substituted by one substituent chosen from the group consisting of F, Cl, —$CF_3$, methyl, hydroxyl, methoxy and —NR(37)R(38);

R(37) and R(38) independently of one another are hydrogen or —$CH_3$;

Y is a bond, oxygen, —S— or —NR(9);

R(9) is hydrogen or methyl;

R(7) is —NR(10)R(11);

R(10) and R(11) independently of one another are hydrogen, —($C_1$–$C_4$)-alkyl, —($C_1$–$C_5$)-alkanoyl, —($C_1$–$C_4$)-alkoxycarbonyl, benzyl or benzyloxycarbonyl;

or

R(10) is trityl;

R(8) is —OR(12) or —NR(12)R(13);

R(12) and R(13) independently of one another are hydrogen, —($C_1$–$C_4$)-alkyl or benzyl;

and the other particular substituents R(2) and R(3) independently of one another are —($C_1$–$C_4$)-alkyl, hydrogen, F or Cl;

R(4) and R(5) independently of one another are hydrogen, methyl, F, Cl, —OR(32), —NR(33)R(34) or —$CF_3$;

R(32), R(33) and R(34) independently of one another are hydrogen or methyl;
and pharmaceutically tolerated salts thereof.

If one of the substituents R(1) to R(5) contains one or more centers of asymmetry, these can be in either the S or the R configuration, independently of one another. The compounds can exist as optical isomers, as diastereomers, as racemates or as mixtures thereof.

The alkyl and perfluoroalkyl radicals described can be either straight-chain or branched.

The invention furthermore relates to a process for the preparation of the compounds I, which comprises reacting compounds of the formula II

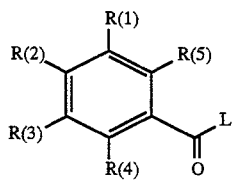

in which R(1) to R(5) have the abovementioned meanings and L is a leaving group which can easily be substituted nucleophilically, with guanidine.

The activated acid derivatives of the formula II in which L is an alkoxy group, preferably a methoxy group or phenoxy group, a phenylthio, methylthio or 2-pyridylthio group or a nitrogen-containing heterocyclic radical, preferably 1-imidazolyl, are advantageously obtained in a manner known per se from the carboxylic acid chlorides on which they are based (formula II, L=Cl), which in turn can be prepared in a manner known per se from the carboxylic acids on which they are based (formula II, L=OH), for example with thionyl chloride. In addition to the carboxylic acid chlorides of the formula II (L=Cl), other activated acid derivatives of the formula II can be prepared in a manner known per se directly from the benzoic acid derivatives on which they are based (formula II, L=OH), for example the methyl esters of the formula II, where L=OCH$_3$, by treatment with gaseous HCl in methanol, the imidazolides of the formula II by treatment with carbonyldiimidazole (L=1-imidazolyl, Staab, Angew. Chem. Int. Ed. Engl. 1,351–367 (1962)), the mixed anhydrides II with Cl—COOC$_2$H$_5$ or tosyl chloride in the presence of triethylamine in an inert solvent, and also the activations of benzoic acids with dicyclohexylcarbodiimide (DCC) or with O-[(cyano (ethoxycarbonyl)-methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden 1991]. A number of suitable methods for the preparation of activated carboxylic acid derivatives of the formula II are mentioned with reference to the source literature in J. March, Advanced Organic Chemistry, Third Edition (John Wiley & Sons, 1985), page 350.

The reaction of an activated carboxylic acid derivative of the formula I with guanidine is carried out in a manner known per se in a protic or aprotic polar but inert organic solvent. For the reaction of the benzoic acid methyl esters (II, L=OMe) with guanidine, methanol, isopropanol or THF at between 20° C. and the boiling point of these solvents have proved appropriate. Most of the reactions of compounds II with salt-free guanidine were advantageously carried out in inert solvents such as THF, dimethoxyethane, dioxane or isopropanol. However, water can also be used as the solvent.

If L is Cl, the reaction is advantageously carried out with the addition of an acid-trapping agent, for example in the form of excess guanidine, to bond the hydro-halic acid.

The unknown compounds of the formula II can be prepared by methods known from the literature, for example by converting 4-halo-3-chlorosulfonylbenzoic acids into 3-aminosulfonyl-4-halo-benzoic acids with ammonia or amines, or into 3-alkylsulfonyl-4-halo-benzoic acids with a weak reducing agent, such as sodium bisulfite, and subsequent alkylation, and reacting the products by one of the process variants described above to give compounds I according to the invention.

The introduction of the phenylalanine derivatives substituted in the phenyl part by sulfur, oxygen or nitrogen nucelophiles is effected by methods known from the literature for nucleophilic substitution on an aromatic. Halides and trifluoromethanesulfonates have proved suitable as the leaving group on the benzoic acid derivative for this substitution. The reaction is advantageously carried out in a dipolar aprotic solvent, such as DMF or TMU, at a temperature of from 0° C. up to the boiling point of the solvent, preferably from 80° C. up to the boiling point of the solvent. An alkali metal salt or alkaline earth metal salt having an anion of high basicity and low nucleophilicity, for example K$_2$CO$_3$ or CsCO$_3$, is advantageously used as the acid-trapping agent. The known standard methods can be chosen for protection of the functional groups of the amino acid. t-Butoxycarbonyl, benzyloxycarbonyl, dibenzyl and trityl have proved suitable on the nitrogen. The acid function can be employed without protection, or a suitable ester or a suitable amide can be used.

The alkyl or aryl substituents are introduced by methods known from the literature of palladium-mediated cross-couplings of aryl halides with, for example, organozinc compounds, organostannanes, organoboron acids or organoboranes.

Benzoylguanidines I are in general weak bases and can bond acid to form salts. Possible acid addition salts are salts of all the pharmacologically tolerated acids, for example halides, in particular hydrochlorides, lactates, sulfates, citrates, tartrates, acetates, phosphates, methylsulfonates and p-toluenesulfonates.

The compounds I are substituted acylguanidines. The most prominent representative of the acylguanidines is the pyrazine derivative amiloride, which is used in treatment as a potassium-saving diuretic. Numerous other compounds of the amiloride type are described in the literature, such as, for example, dimethylamiloride or ethylisopropylamiloride.

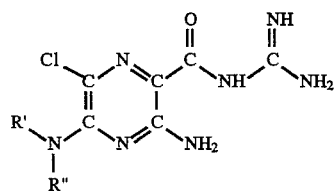

Amiloride: R', R"=H
dimethylamiloride: R', R"=CH$_3$
ethylisopropylamiloride: R'=C$_2$H$_5$, R"=CH(CH$_3$)$_2$ Studies have furthermore been disclosed which indicate antiarrhythmic properties of amiloride [Circulation 79, 1257–63 (1989)]. However, the facts that this effect is only weak and occurs accompanied by an antihypertensive and saluretic action, and that these side-effects are undesirable for the treatment of disturbances in cardiac rhythm, oppose widespread use as an antiarrhythmic.

Indications of antiarrhythmic properties of amiloride have also been obtained in experiments on isolated animal hearts [Eur. Heart J. 9 (suppl. 1): 167 (1988) (book of abstracts)].

Thus, for example, it was found on rat hearts that an artificially induced ventricular fibrillation could be suppressed completely by amiloride. The abovementioned amiloride derivative ethylisopropylamiloride was even more potent than amiloride in this model.

Benzoylguanidines which carry a hydrogen atom in the position corresponding to the radicals R(1), R(4) and R(5) are described in U.S. Pat. No. 5,091,394. European Laid-Open Specification 0 556 674 (HOE 92/F 034) describes benzoylguanidines in which, however, the substituents do not have the meanings claimed according to the present invention. No derivatives of amino acids are described. Furthermore, the water-solubility of these known benzoylguanidines leaves something to be desired.

Acylguanidines which are structurally similar to the compounds of the formula I and are derived from commercially available loop diuretics, such as bumetanide are claimed in U.S. Pat. No. 3,780,027. A potent salidiuretic activity is reported correspondingly for these compounds.

It was therefore surprising that the compounds according to the invention have no undesirable and adverse salidiuretic properties but very good antiarrhythmic properties which are important for the treatment of diseases such as occur, for example, with oxygen deficiency symptoms. Because of their pharmacological properties, the compounds are outstandingly suitable as antiarrhythmic medicaments having a cardioprotective component for prophylaxis of infarction and infarction treatment and for treatment of angina pectoris, where they also preventively inhibit or greatly reduce the pathophysiological processes during the formation of ischemically induced damage, especially during triggering of ischemically induced cardiac arrhythmias. Because of their protective actions against pathological hypoxic and ischemic situations, the compounds of the formula I according to the invention can be used, as a result of inhibition of the cellular $Na^+/H^+$ exchange mechanism, as medicaments for the treatment of all acute or chronic damage caused by ischemia or diseases thereby induced primarily or secondarily. This applies to their use as medicaments for surgical operations, for example during organ transplants, where the compounds can be used both to protect the organs in the donor before and during removal, to protect removed organs, for example during treatment with or storage thereof in physiological bath fluids, and during transfer to the recipient organism. The compounds are likewise valuable medicaments which have a protective action while angioplastic surgical operations are carried out, for example on the heart and also on peripheral vessels. In accordance with their protective action against ischemically induced damage, the compounds are also suitable as medicaments for the treatment of ischemias of the nervous system, in particular of the CNS, where they are suitable, for example, for treatment of apoplexy or cerebral edema. The compounds of the formula I according to the invention furthermore are likewise suitable for treatments of forms of shock, such as, for example allergic, cardiogenic, hyporolemic and bacterial shock.

The compounds of the formula I according to the invention furthermore are distinguished by a potent inhibiting action on the proliferation of cells, for example fibroblast cell proliferation and proliferation of the smooth vascular muscle cells. The compounds of the formula I are thus suitable as valuable therapeutics for diseases in which cell proliferation is a primary or secondary cause, and they can therefore be used as antiatherosclerotics and agents against late diabetic complications, carcinoses, fibrotic diseases, such as pulmonary fibrosis, hepatic fibrosis or renal fibrosis, and organ hypertrophies and hyperplasias, in particular for prostate hyperplasia or prostate hypertrophy.

The compounds according to the invention are effective inhibitors of the cellular sodium/proton antiporter ($Na^+/H^+$ exchanger), which, with numerous diseases (essential hypertension, atherosclerosis, diabetes and the like) is also increased in those cells which are readily accessible for measurements, such as, for example, in erythrocytes, platelets or leukocytes. The compounds according to the invention are therefore suitable as outstanding and simple scientific tools, for example in their use as diagnostic agents for determination of and differentiation between forms of hypertension, and also of atherosclerosis, diabetes, proliferative diseases and the like. The compounds of the formula I are also suitable for preventive treatment to impede the genesis of high blood pressure, for example essential hypertension.

Compared with the known compounds, the compounds according to the invention display a significantly improved water-solubility. They are therefore considerably more suitable for intravenous administration.

Medicaments which comprise a compound I can be administered here orally, parenterally, intravenously or rectally or by inhalation, the preferred administration depending on the particular clinical picture of the disease. The compounds I can be used here by themselves or together with pharmaceutical auxiliaries, both in veteri-nary and in human medicine.

The expert is familiar with the auxiliaries which are suitable for the desired medicament formulation on the basis of his expert knowledge. In addition to solvents, gel-forming agents, suppository bases, tablet-making auxiliaries and other excipients for active ingredients, it is possible to use, for example, antioxidants, dispersing agents, emulsifiers, defoamers, flavor correctants, preservatives, solubilizing agents or dyestuffs.

For an oral use form, the active compounds are mixed with the additives suitable for this purpose, such as excipients, stabilizers or inert diluents, and are brought into the suitable dosage forms, such as tablets, coated tablets, suppository capsules and aqueous, alcoholic or oily solutions, by the customary methods. Inert excipients which can be used are, for example, gum arabic, magnesia, magnesium carbonate, potassium phosphate, lactose, glucose or starch, in particular corn starch. Formulation can take place both as dry granules and as moist granules. Possible oily excipients or solvents are, for example, vegetable or animal oils, such as sunflower oil or cod-liver oil.

For subcutaneous or intravenous administration, the active compounds are dissolved, suspended or emulsified, if desired, with the substances customary for this purpose, such as solubilizing agents, emulsifiers or other auxiliaries. Possible solvents are, for example: water, physiological saline solution or alcohols, for example ethanol, propanol and glycerol and in addition also sugar solutions, such as glucose solutions or mannitol solutions, or also a mixture of the various solvents mentioned.

Pharmaceutical formulations which are suitable for administration in the form of aerosols or sprays are, for example, solutions, suspensions or emulsions of the active compound of the formula I in a pharmaceutically acceptable solvent, such as, in particular, example, ethanol or water, or a mixture of such solvents. If required, the formulation can also comprise other pharmaceutical auxiliaries, such as surfactants, emulsifiers and stabilizers, as well as a propellent gas. Such a formulation usually comprises the active compound in a concentration of about 0.1 to 10, in particular about 0.3 to 3%, by weight.

The dosage of the active compound of the formula I to be administered and the frequency of the administration depend on the action potency and duration of the action of the compounds used; and, furthermore, also on the nature and severity of the disease to be treated and on the sex, age, weight and individual responsiveness of the mammal to be treated.

The daily dose of a compound of the formula I for a patient weighing about 75 kg is on average at least 0.001 mg/kg of body weight, preferably at least 0.01 mg/kg of body weight, to not more than 10 mg/kg of body weight, preferably to not more than 1 mg/kg of body weight. For acute outbreaks of the disease, for example immediately after a cardiac infarction has been suffered, even higher and above all more frequent dosages may also be necessary, for example up to 4 individual doses per day. Up to 100 mg per day may be necessary for intravenous use in particular, for example for an infarction patient on the intensive care ward.

List of abbreviations:

| | |
|---|---|
| MeOH | Methanol |
| DMF | N,N-Dimethylformamide |
| TMU | N,N,N',N'-Tetramethylurea |
| NBS | N-Bromosuccinimide |
| AIBN | α,α-Azo-bis-isobutyronitrile |
| EI | Electron impact |
| DCI | Desorption/chemical ionization |
| RT | Room temperature |
| EA | Ethyl acetate (EtOAc) |
| DIP | Diisopropyl ether |
| MTB | Methyl tert-butyl ether |
| mp | Melting point |
| HEP | n-Heptane |
| DME | Dimethoxyethane |
| FAB | Fast atom bombardment |
| $CH_2Cl_2$ | Methylene chloride |
| THF | Tetrahydrofuran |
| eq | Equivalent |
| ES | Electrospray ionization |
| Me | Methyl |
| Et | Ethyl |
| Bn | Benzyl |
| CNS | Central nervous system |
| Brine | Saturated aqueous NaCl solution |

Experimental section

General instructions for the preparation of benzoylguanidines (I)

Variant A: from benzoic acids (II, L=OH)

0.01 mol of the benzoic acid derivative of the formula II is dissolved or suspended in 60 ml of anhydrous THF, and 1.78 g (0.011 mol) of carbonyldiimidazole are then added. After the mixture has been stirred at RT for 2 hours, 2.95 g (0.05M) of guanidine are introduced into the reaction solution. After the mixture has been stirred overnight, the THF is distilled off under reduced pressure (rotary evaporator), water is added, the pH is brought to 6 to 7 with 2N HCl and the corresponding benzoylguanidine (formula I) is filtered off. The benzoylguanidines thus obtained can be converted into the corresponding salts by treatment with aqueous, methanolic or ethereal hydrochloric acid or other pharmacologically tolerated acids.

General instructions for preparation of benzoylguanidines (I)

Variant B: from benzoic acid alkyl esters (II, L=O-alkyl)

5 mmol of the benzoic acid alkyl ester of the formula II and 25 mmol of guanidine (free base) are dissolved in 15 ml of isopropanol or suspended in 15 ml of THF and the solution or suspension is boiled under reflux until conversion is complete (thin layer monitoring; typical reaction time 2 to 5 hours). The solvent is distilled off under reduced pressure (rotary evaporator), the residue is taken up in 300 ml of EA and the mixture is washed 3 times with 50 ml of $NaHCO_3$ solution each time. It is dried over $Na_2SO_4$, the solvent is distilled off in vacuo and the residue is chromatographed over silica gel using a suitable mobile solvent, for example EA/MeOH 5:1. (For salt formation, cf. Variant A)

EXAMPLE 1

N-tert-Butoxycarbonyl-4-[(4-guanidinocarbonyl-2-methylsulfonyl)phenoxy]-phenylalanine

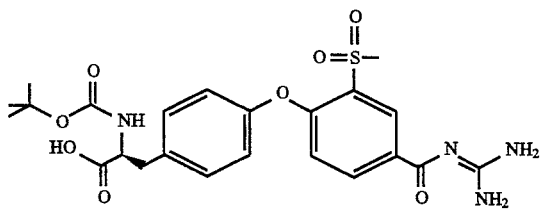

1.8 g of N-tert-butoxycarbonyl-4-[(4-methoxycarbonyl-2-methylsulfonyl)phenoxy]-phenylalanine and 1.1 g of guanidine are reacted in accordance with Variant B to give 700 mg of a colorless solid. mp>270° C. $R_f$ (acetone/water 10:1)=0.37 MS (FAB): 521 (M+H)⁺ a) N-tert-butoxycarbonyl-4-[(4-methoxycarbonyl-2-methylsulfonyl)phenoxy]-phenylalanine 4.5 g of N-tert-butoxycarbonyl-4-[(4-methoxycarbonyl-2-methylsulfonyl)phenoxy]-phenylalanine benzyl ester and 500 mg of 10% Pd/C are hydrogenated in 50 ml of MeOH under a normal pressure of hydrogen for 20 hours. The catalyst is then filtered off and the solvent is removed in vacuo and chromatographed with EA/MeOH 10:1. 2.1 g of a colorless viscous oil are obtained. $R_f$ (EA/MeOH 10:1)= 0.12 MS (DCI): 494 (M+H)⁺ b) N-tert-butoxycarbonyl-4-([4-methoxycarbonyl-2-methylsulfonyl)phenoxy]-phenylalanine benzyl ester 2.8 g of N-tert-butoxycarbonyl-tyrosine benzyl ester, 2.2 g of 4-fluoro-3-trifluoromethylbenzoic acid methyl ester and 4.0 g of $K_2CO_3$ are stirred in 100 ml of DMF (anhydrous) at 110° C. for 45 minutes. The reaction mixture is poured into 500 ml of water, the pH is brought to 2 with $NaHSO_4$ and the mixture is extracted 3 times with 200 ml of EA each time. The extract is dried over $Na_2SO_4$ and the solvent is removed in vacuo. 4.2 g of a colorless oil. $R_f$(DIP)=0.12 MS (ES): 584 (M+H)⁺

EXAMPLE 2

4-[(4-Guanidinocarbonyl-2-methylsulfonyl)phenoxy]phenylalanine

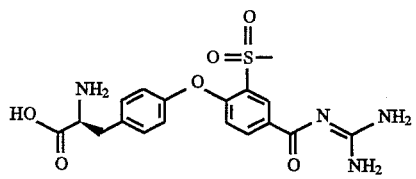

170 mg of the title compound of Example 1 are suspended in 5 ml of $CH_2Cl_2$, and 61 μl of trifluoromethanesulfonic acid are added at RT. The mixture is stirred at this temperature for 90 minutes, and then poured into 50 ml of saturated, aqueous $K_2HPO_4$ solution. It is then extracted 3 times with 100 ml of EA, the extracts are dried over $Na_2SO_4$ and the solvent is removed in vacuo. 125 mg of an amorphous solid are obtained. R_f (EA/MeOH 1:1)=0.43 MS (ES): 421 (M+H)⁺

EXAMPLE 3

N-tert-Butoxycarbonyl-4-[(4-guanidinocarbonyl-2-trifluoromethyl)phenoxy]phenylalanine

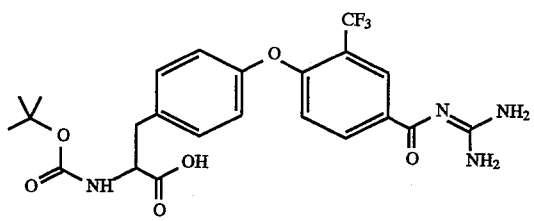

3.5 g of N-tert-butoxycarbonyl-4-[(4-methoxycarbonyl-2-trifluoromethyl)phenoxy]phenylalanine are guanylated with 2.2 g of guanidine in 10 ml of isopropanol according to variant B. 1.68 g of a colorless solid are obtained, mp 231° C. R_f (acetone/water 20:1)=0.30 MS (FAB): 512 (M+H)⁺ a) N-tert-butoxycarbonyl-4-[(4-methoxycarbonyl-2-trifluoromethyl)phenoxy]phenylalanine 4.6 g of N-tert-butoxycarbonyl-4-[(4-methoxycarbonyl-2-trifluoromethyl)phenoxy]phenylalanine benzyl ester and 860 mg of 10% Pd on active charcoal (water content 50%) are stirred in 100 ml of MeOH under H₂ under atmospheric pressure for 24 h at RT. The catalyst is then filtered off and the volatile constituents are removed in vacuo. 3.5 g of a colorless oil are obtained. R_f (EA/MeOH 10:1)=0.10 MS (ES): 484 (M+H)⁺ b) N-tert-butoxycarbonyl-4-[(4-methoxycarbonyl-2-trifluoromethyl)phenoxy]phenylalanine benzyl ester 4.0 g of Boc-Tyr-OBn, 2.4 g of methyl 4-fluoro-3-trifluoromethylbenzoate and 7.0 g of Cs₂CO₃ are stirred in 30 ml of anhydrous tetramethylurea at 110° C. for 2 h. The mixture is cooled, diluted with 800 ml of EA and washed with 3×100 ml of water and with 3×100 ml of saturated aqueous NaCl solution. The organic phase is dried over Na₂SO₄, and the solvents are removed in vacuo. Chromatography on silica gel with DIP gives 4.6 g of a colorless oil. R_f (DIP)=0.41 MS (FAB): 574 (M+H)⁺

EXAMPLE 4

4-[(4-Guanidinocarbonyl-2-trifluoromethyl)phenoxy]phenylalanine, dihydrochloride

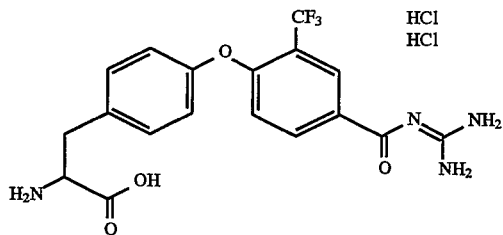

0.8 g of N-tert-butoxycarbonyl-4-[(4-guanidinocarbonyl-2-trifluoromethyl)phenoxy]phenylalanine are dissolved in 50 ml of CH₂Cl₂, and 277 μl of trifluoromethanesulfonic acid are added at 0° C. The mixture is allowed to rise to RT, during which a lumpy precipitate is formed. The mixture is diluted with 50 ml of DME and then stirred at RT for 1 h. The solvents are removed in vacuo, the residue is taken up in 15 ml of water, and the mixture is adjusted to a pH of 7 with saturated aqueous NaHCO₃ solution. The precipitate which forms is filtered off and chromatographed on silica gel with CH₂Cl₂/MeOH/H₂O/HOAc 8:4:1:1.The product is dissolved in 2 ml of 4N HCl, and the volatile constituents are removed in vacuo. 100 mg of colorless crystals are obtained, mp 245° C. R_f (CH₂Cl₂/MeOH/H₂O/HOAc 8:4:1:1)=0.27 MS (FAB): 411 (M+H)⁺

EXAMPLE 5

N-tert-Butoxycarbonyl-4-[(guanidinocarbonyl-2-acetyl)phenoxy]phenylalanine

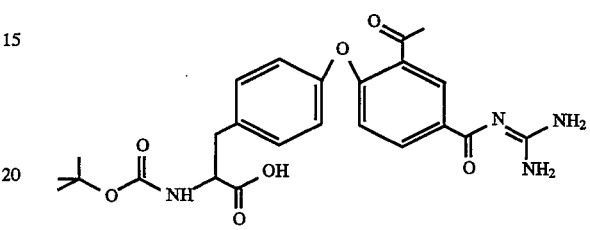

350 mg of N-tert-butoxycarbonyl-4-[(4-n-butoxycarbonyl-2-acetyl)phenoxy]phenylalanine are guanylated with 200 mg of guanidine in 2 ml of isopropanol according to variant B. 170 mg of a colorless amorphous solid are obtained. R_f (acetone/water 20:1)=0.20 MS (FAB): 485 (M+H)⁺ a) N-tert-butoxycarbonyl-4-[(4-n-butoxycarbonyl-2-acetyl)phenoxy]phenylalanine 460 mg of N-tert-butoxycarbonyl-4-[(4-n-butoxycarbonyl-2-acetyl)phenoxy]phenylalanine benzyl ester and 86 mg of 10% Pd on active charcoal (water content 50%) are stirred in 10 ml of MeOH under H₂ at atmospheric pressure for 24 h at RT. The catalyst is then filtered off and the volatile constituents are removed in vacuo. 350 mg of a colorless oil are obtained. R_f (EA/MeOH 5:1)=0.10 MS (ES): 500 (M+H)⁺ b) N-tert-butoxycarbonyl-4-[(4-n-butoxycarbonyl-2-acetyl)phenoxy]phenylalanine benzyl ester 8.1 g of Boc-Tyr-OBn, 5.1 g of N-butyl 4-fluoro-3-acetylbenzoate and 14.2 g of Cs₂CO₃ are stirred in 60 ml of anhydrous N-methylpyrrolidone at 110° C. for 2 h. The mixture is cooled, diluted with 1 l of EA and washed with 1×200 ml of water and 3×100 ml of saturated aqueous NaCl solution. The organic phase is dried over Na₂SO₄ and the solvents are removed in vacuo. Chromatography on silica gel with DIP gives 8.6 g of a colorless oil. R_f (DIP)=0.25 MS (FAB): 590 (M+H)⁺ c) n-Butyl 4-fluoro-3-acetylbenzoate 12.4 g of 2-fluoro-5-bromacetophenone, 30 ml of tri-n-butylamine, 5.6 g of palladium(II) acetate and 10 g of 1,3-bis(diphenylphosphino)propane are stirred in 80 ml of n-butanol and 160 ml of DMF at 110° C. for 3 h. The mixture is then cooled to RT and the volatile constituents are removed in vacuo. The residue is taken up in 1 l of EA, the palladium-containing residue is filtered off, and the filtrate is washed with twice 500 ml of 5% aqueous NaHSO₄ solution and once with 500 ml of water. The mixture is dried over Na₂SO₄, the solvent is removed in vacuo and the residue is chromatographed on silica gel of EA/HEP 1:4. 7.8 g of a colorless oil are obtained. R_f (EA/HEP 1:4)=0.59 MS (EI): 239 (M+H)⁺ d) 2-Fluoro-5-bromacetophenone 20 g of 2-fluoroacetophenone are dissolved in 76 ml of 96% H₂SO₄, and a solution of 20 g of dibromocyanuric acid in 230 ml of 96% $H_2SO_4$ is added dropwise at RT. The mixture is stirred at RT for 1 h, then poured onto 1 kg of ice and extracted with 3 times 200 ml of $CH_2Cl_2$. The mixture is dried over $Na_2SO_4$ and the solvent is removed in vacuo. The residue is subjected to fractional distillation, to give 12.4 g of a colorless oil having a boiling point of 70° C. (2 mbar). $R_f$ ($CH_2Cl_2$)=0.53 MS (ES): 217 (M+H)$^+$

EXAMPLE 6

4-[(4-Guanidinocarbonyl-2-acetyl)phenoxy] phenylalanine, dihydrochloride

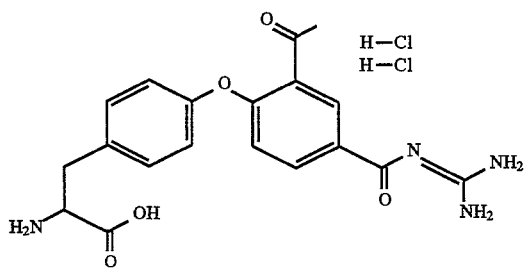

80 mg of N-tert-butoxycarbonyl-4-[(4-guanidinocarbonyl-2-acetyl)phenoxy]phenylalanine are dissolved in 5 ml of $CH_2Cl_2$, and 28 μl of trifluoromethanesulfonic acid are added at 0° C. The mixture is allowed to rise to RT, during which a lumpy precipitate is formed. The mixture is diluted with 5 ml of DME, then stirred at RT for 1 h. The solvents are removed in vacuo, the residue is taken up in 5 ml of water and the mixture is adjusted to a pH of 7 with saturated aqueous $NaHCO_3$ solution. The precipitate which forms is filtered off and chromatographed on silica gel with $CH_2Cl_2$/MeOH/$H_2O$/HOAc 8:4:1:1. The product is dissolved in 2 ml of 4N HCl and the volatile constituents are removed in vacuo. 40 mg of colorless crystals are obtained, mp 210° C. (decomposition). $R_f$ ($CH_2Cl_2$/MeOH/$H_2O$/HOAc 8:4:1:1)=0.20 MS (FAB): 385 (M+H)$^+$

EXAMPLE 7

N-tert-Butoxycarbonyl-4-[(4-guanidinocarbonyl-2-isopropyl)phenoxy]phenylalanine

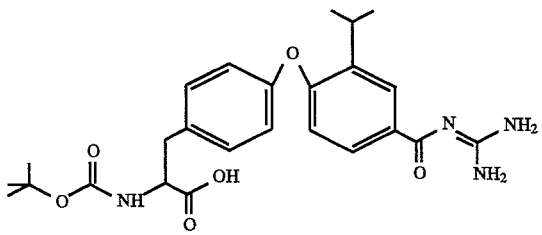

1.75 g of N-tert-butoxycarbonyl-4-[(4-n-butoxycarbonyl-2-isopropyl)phenoxy]phenylalanine are guanylated with 1.0 g of guanidine in 10 ml of isopropanol according to variant B. 950 mg of a colorless amorphous solid are obtained. $R_f$ (acetone/water 20:1)=0.25 MS (FAB): 485 (M+H)$^+$ a) N-tert-butoxycarbonyl-4-[(4-n-butoxycarbonyl-2-isopropyl)phenoxy]phenylalanine 2.3 g of N-tert-butoxycarbonyl-4-[(4-n-butoxycarbonyl-2-isopropenyl)phenoxy]phenylalanine benzyl ester and 400 mg of 10% Pd on active charcoal (water content 50%) are stirred in 50 ml of MeOH under $H_2$ under atmospheric pressure for 24 h at RT. The catalyst is then filtered off and the volatile constituents are removed in vacuo. 1.80 g of a colorless oil are obtained. $R_f$ (EA/MeOH 10:1)=0.10 MS (ES): 500 (M+H)$^+$ b) N-tert-butoxycarbonyl-4-[(4-n-butoxycarbonyl-2-isopropenyl)phenoxy]phenylalanine benzyl ester 4.2 g of methyltriphenylphosphonium iodide are suspended in 100 ml of THF, 1.2 g of potassium tert-butylate are added and the mixture is stirred at RT for 3 h. A solution of 5.9 g of N-tert-butoxycarbonyl-4-[(4-n-butoxycarbonyl-2-acetyl)phenoxy]phenylalanine benzyl ester in 50 ml of THF is then injected, and the mixture is stirred at RT for 30 minutes. The reaction mixture is then poured into 100 ml of saturated aqueous $NaHCO_3$ solution and extracted with 3 times 100 ml of EA. The extracts are dried over $Na_2SO_4$, the solvent is removed in vacuo and the residue is chromatographed on silica gel with DIP. 2.7 g of a colorless oil are obtained. $R_f$ (DIP)=0.35 MS (FAB): 588 (M+H)$^+$

EXAMPLE 8

4-[(4-Guanidinocarbonyl-2-isopropyl)phenoxy] phenylalanine, dihydrochloride

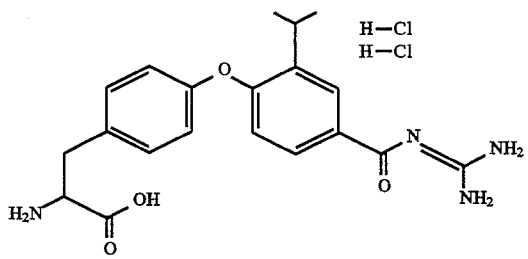

800 mg of N-tert-butoxycarbonyl-4-[(4-guanidinocarbonyl-2-isopropyl)phenoxy]phenylalanine are dissolved in 50 ml of $CH_2Cl_2$, and 280 μl of trifluoromethanesulfonic acid are added at 0° C. The mixture is allowed to rise to RT, during which a lumpy precipitate is formed. The mixture is diluted with 50 ml of DME, then stirred at RT for 1 h. The solvents are removed in vacuo, the residue is taken up in 50 ml of water and the mixture is adjusted to a pH of 7 with saturated aqueous $NaHCO_3$ solution. The precipitate which forms is filtered off and chromatographed on silica gel with $CH_2Cl_2$/MeOH/$H_2O$/HOAc 8:4:1:1. The product is dissolved in 20 ml of 4N HCl and the volatile constituents are removed in vacuo. 320 mg of colorless crystals are obtained, m.p. 230° C. (decomposition). $R_f$ ($CH_2Cl_2$/MeOH/$H_2O$/HOAc 8:4:1:1)= 0.30 MS (FAB): 385 (M+H)$^+$ Pharmacological data:

Inhibition of the Na+/H$^+$ exchanger of rabbit erythrocytes

White New Zealand rabbits (Ivanovas) were given a standard diet with 2% of cholesterol for six weeks in order to activate the Na$^+$/H$^+$ exchange and in this way to be able to determine the Na$^+$ influx into the erythrocytes via Na$^+$/H$^+$ exchange by flame photometry. The blood was removed from the ear arteries and rendered noncoagulable by 25 IU of potassium-heparin. A portion of each sample was used for duplicate determination of the hematocrit by centrifugation. Aliquots of in each case 100 μl were used for measurement of the starting Na$^+$ content of the erythrocytes.

To determine the amiloride-sensitive sodium influx, 100 μl of each blood sample were incubated in 5 ml portions each of a hyperosmolar salt/sucrose medium (mmol/l: 140 NaCl, 3 KCl, 150 sucrose, 0.1 ouabain, 20 tris-hydroxymethylaminomethane) at pH 7.4 and 37° C. The erythrocytes were then washed three times with ice-cold MgCl₂/ouabain solution (mmol/l: 112 MgCl₂, 0.1 ouabain) and hemolyzed in 2.0 ml of distilled water. The intracellular sodium content was determined by flame photometry.

The Na⁺ net influx was calculated from the difference between the starting sodium values and the sodium content of the erythrocytes after incubation. The sodium influx which can be inhibited by amiloride resulted from the difference between the sodium content of the erythrocytes after incubation with and without 3×10⁻⁴ mol/l of amiloride. This procedure was also followed with compounds according to the invention.

Results

Inhibition of the Na⁺/H⁺ Exchanger

| Example | IC₅₀ µmol/l |
|---------|-------------|
| 1 | 0.43 |
| 2 | 1.0 |
| 4 | 0.026 |

We claim:
1. A compound of the formula I

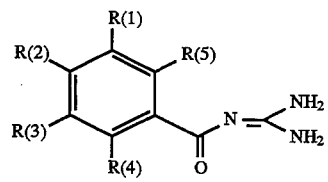

in which:
one of the three substituents R(1), R(2) and R(3) is
—Y—[4-[(CH₂)$_k$—CHR(7)—(C═O)R(8)]phenyl],
—Y—[3-[(CH₂)$_k$—CHR(7)—(C═O)R(8)]phenyl] or
—Y—[2-[(CH₂)$_k$—CHR(7)—(C═O)R(8)]phenyl], in which the phenyl is in each case unsubstituted or substituted by 1–2 substituents from the group consisting of F, Cl, —CF₃, methyl, hydroxyl, methoxy and —NR(37)R(38);

R(37) and R(38) independently of one another are hydrogen or —CH₃;

Y is a bond, oxygen, —S— or —NR(9);

R(9) is hydrogen or —(C₁–C₄)-alkyl;

R(7) is —OR(10) or —NR(10)R(11);

R(10) and R(11) independently of one another are hydrogen, —(C₁–C₈)-alkyl, —(C₁–C₈)-alkanoyl, —(C₁–C₈)-alkoxycarbonyl, benzyl, benzyloxycarbonyl;

or

R(10) is trityl;

R(8) is —OR(12) or —NR(12)R(13);

R(12) and R(13) independently of one another are hydrogen, —(C₁–C₈)-alkyl or benzyl;

k is zero, 1, 2, 3 or 4;

and the other particular radicals R(1), R(2) and R(3) independently of one another are —(C₁–C₈)-alkyl, —(C₂–C₈)-alkenyl or —(CH₂)$_m$R(14);

m is zero, 1 or 2;

R(14) is —(C₃–C₈)-cycloalkyl or phenyl, which is unsubstituted or substituted by 1–3 substituents chosen from the group consisting of F, Cl, —CF₃, methyl, methoxy and —NR(15)R(16);

R(15) and R(16) are hydrogen or —CH₃;

or the other particular radicals R(1), R(2) and R(3) independently of one another are R(18)R(19)N—C═Y')— NH—SO₂—;

Y' is oxygen, —S— or —N—R(20);

R(18) and R(19) independently of one another are hydrogen, —(C₁–C₈)-alkyl, —(C₃–C₆)-alkenyl or —(CH₂)$_t$—R(21);

t is zero, 1, 2, 3 or 4;

R(21) is —(C₅–C₇)-cycloalkyl or phenyl, which is unsubstituted or substituted by 1–3 substituents chosen from the group consisting of F, Cl, —CF₃, methoxy and —(C₁–C₄)-alkyl;

or

R(18) and R(19) together are 4 or 5 methylene groups, one CH₂ group of which can be replaced by oxygen, —S—, —NH—, —N—CH₃ or —N-benzyl;

R(20) is as defined for R(18) or amidine;

or the other particular radicals R(1), R(2) and R(3) independently of one another are hydrogen, F, Cl, Br, I, —C≡N, X—(CH₂)$_p$—(C$_q$F$_{2q+1}$), R(22)—SO$_u$—, R(23)R(24)N—CO—, R(25)—CO— or R(26)R(27) N—SO₂—, in which the perfluoroalkyl group is straight-chain or branched;

X is a bond, oxygen, —S— or —NR(28);

u is zero, 1 or 2;

p is zero, 1 or 2;

q is 1, 2, 3, 4, 5 or 6;

R(22), R(23), R(25) and R(26) independently of one another are —(C₁–C₈)-alkyl, —(C₃–C₆)-alkenyl, —(CH₂)$_n$—R(29) or —CF₃;

n is zero, 1, 2, 3 or 4;

R(28) is hydrogen or —(C₁–C₃)-alkyl;

R(29) is —(C₃–C₇)-cycloalkyl or phenyl, which is unsubstituted or substituted by 1–3 substituents chosen from the group consisting of F, Cl, —CF₃, methyl, methoxy and —NR(30)R(31);

R(30) and R(31) are hydrogen or —(C₁–C₄)-alkyl;

or

R(23), R(25) and R(26) are hydrogen;

R(24) and R(27) independently of one another are hydrogen or —(C₁–C₄)-alkyl;

or

R(23) and R(24), and R(26) and R(27), together are 4 or 5 methylene groups, one CH₂ group of which can be replaced by oxygen, —S—, —NH—, —N—CH₃ or —N-benzyl;

or the other particular radicals R(1), R(2) and R(3) independently of one another are —OR(35) or —NR(35)R(36);

R(35) and R(36) independently of one another are hydrogen or —(C₁–C₆)-alkyl;

or

R(35) and R(36) together are 4–7 methylene groups, one CH₂ group of which can be replaced by oxygen, —S—, —NH—, —N—CH₃ or —N-benzyl;

R(4) and R(5) independently of one another are hydrogen, —(C₁–C₄)-alkyl, F, Cl, —OR(32), —NR(33)R(34) or —C$_r$F$_{2r+1}$;

R(32), R(33) and R(34) independently of one another are hydrogen or —(C₁–C₃)-alkyl;

r is 1, 2, 3 or 4;

or a pharmaceutically tolerated salt thereof.

2. A compound of the formula I as claimed in claim 1, in which:

R(1) is —($C_1$–$C_4$)-alkyl, —($C_2$–$C_4$)-alkenyl or —$(CH_2)_m$R(14);

m is zero, 1 or 2;

R(14) is —($C_5$–$C_6$)-cycloalkyl or phenyl, which is unsubstituted or substituted by 1–2 substituents chosen from the group consisting of F, Cl, —$CF_3$, methyl, methoxy and —NR(15)R(16);

R(15) and R(16) independently of one another are hydrogen or —$CH_3$;

or

R(1) is R(18)R(19)N—(C=Y')—NH—$SO_2$—;

Y' is oxygen, —S— or —N—R(20);

R(18) and R(19) independently of one another are hydrogen, —($C_1$–$C_4$)-alkyl, —($C_3$–$C_4$)-alkenyl or —$(CH_2)_t$—R(21);

t is zero, 1 or 2;

R(21) is —($C_5$–$C_6$)-cycloalkyl or phenyl, which is unsubstituted or substituted by 1–2 substituents chosen from the group consisting of F, Cl, —$CF_3$, methoxy and methyl;

or

R(18) and R(19) together are 4 or 5 methylene groups, one $CH_2$ group of which can be replaced by oxygen, —S—, —NH—, —N—$CH_3$ or —N-benzyl;

R(20) is as defined for R(18) or amidine;

or

R(1) is hydrogen, F, Cl, Br, I, —C≡N, R(22)—$SO_2$—, R(23)R(24)N—CO—, R(25)—CO— or R(26)R(27)N—$SO_2$—;

R(22), R(23), R(25) and R(26) independently of one another are —($C_1$–$C_4$)-alkyl, —($C_3$–$C_4$)-alkenyl, —$(CH_2)_n$—R(29) or —$CF_3$;

n is zero, 1 or 2;

R(29) is —($C_5$–$C_6$)-cycloalkyl or phenyl, which is unsubstituted or substituted by 1–2 substituents chosen from the group consisting of F, Cl, —$CF_3$, methyl, methoxy and —NR(30)R(31);

R(30) and R(31) independently of one another are hydrogen or methyl;

or

R(23), R(25) and R(26) are hydrogen;

R(24) and R(27) independently of one another are hydrogen or methyl;

or

R(23) and (R24), and R(26) and R(27), together are 4 or 5 methylene groups, one $CH_2$ group of which can be replaced by oxygen, —S—, —NH—, —N—$CH_3$ or —N-benzyl;

or

R(1) is —OR(35) or —NR(35)R(36);

R(35) and R(36) independently of one another are hydrogen or —($C_1$–$C_4$)-alkyl;

or

R(35) and R(36) together are 4–5 methylene groups, one $CH_2$ group of which can be replaced by oxygen, —S—, —NH—, —N—$CH_3$ or —N-benzyl;

one of the substituents R(2) or R(3) is —Y—[4-[$(CH_2)_k$—CHR(7)—(C=O)R(8)]phenyl], —Y—[3-[$(CH_2)_k$—CHR(7)—(C=O)R(8)]phenyl] or —Y—[2-[$(CH_2)_k$—CHR(7)—(C=O)R(8)]phenyl], in which the phenyl is in each case unsubstituted or substituted by 1–2 substituents from the group consisting of F, Cl, —$CF_3$, methyl, hydroxyl, methoxy or —NR(37)R(38);

R(37) and R(38) independently of one another are hydrogen or —$CH_3$;

Y is a bond, oxygen, —S— or —NR(9);

R(9) is hydrogen or methyl;

R(7) is —OR(10) or —NR(10)R(11);

R(10) and R(11) independently of one another are hydrogen, —($C_1$–$C_5$)-alkyl, —($C_1$–$C_5$)-alkanoyl, —($C_1$–$C_4$)-alkoxycarbonyl, benzyl or benzyloxycarbonyl;

or

R(10) is trityl;

R(8) is —OR(12) or —NR(12)R(13);

R(12) and R(13) independently of one another are hydrogen, —($C_1$–$C_4$)-alkyl or benzyl;

k is zero, 1 or 2;

and the other particular substituents R(2) and R(3) independently of one another are —($C_1$–$C_4$)-alkyl, hydrogen, F, Cl, Br or I;

R(4) and R(5) independently of one another are hydrogen, methyl, F, Cl, —OR(32), —NR(33)R(34) or —$CF_3$;

R(32), R(33) and R(34) independently of one another are hydrogen or methyl.

3. A compound of the formula I as claimed in claim 1, in which:

R(1) is —($C_1$–$C_4$)-alkyl, —($C_2$–$C_4$)-alkenyl or —$(CH_2)_m$R(14);

m is zero, 1 or 2;

R(14) is —($C_5$–$C_6$)-cycloalkyl or phenyl, which is unsubstituted or substituted by 1–2 substituents chosen from the group consisting of F, Cl, —$CF_3$, methyl, methoxy and —NR(15)R(16);

R(15) and R(16) independently of one another are hydrogen or —$CH_3$;

or

R(1) is hydrogen, F, Cl, Br, I, —C≡N, R(22) —$SO_2$—, R(23)R(24)N—CO—, R(25)—CO— or R(26)R(27)N—$SO_2$—;

R(22), R(23), R(25) and R(26) independently of one another are methyl or —$CF_3$, or R(23), R(25) and R(26) are hydrogen;

R(24) and R(27) independently of one another are hydrogen or methyl;

or

R(1) is —OR(35) or —NR(35)R(36);

R(35) and R(36) independently of one another are hydrogen or —($C_1$–$C_4$)-alkyl;

or

R(35) and R(36) together are 4–5 methylene groups, one $CH_2$ group of which can be replaced by oxygen, —S—, —NH—, —N—$CH_3$ or —N-benzyl;

one of the substituents R(2) and R(3) is —Y—[4-[$(CH_2)_k$—CHR(7)—(C=O)R(8)]phenyl], —Y—[3-[$(CH_2)_k$—CHR(7)—(C=O)R(8)]phenyl] or —Y—[2-[$(CH_2)_k$—CHR(7)—(C=O)R(8)]phenyl], in which the phenyl is in each case unsubstituted or substituted by one substituent chosen from the group consisting of F, Cl, —$CF_3$, methyl, hydroxyl, methoxy and —NR(37)R(38);

R(37) and R(38) independently of one another are hydrogen or —CH$_3$;

Y is a bond, oxygen, —S— or —NR(9);

R(9) is hydrogen or methyl;

R(7) is —NR(10)R(11);

R(10) and R(11) independently of one another are hydrogen, —(C$_1$-C$_4$)-alkyl, —(C$_1$-C$_5$)-alkanoyl, —(C$_1$-C$_4$)-alkoxycarbonyl, benzyl or benzyloxycarbonyl;

or

R(10) is trityl;

R(8) is —OR(12) or —NR(12)R(13);

R(12) and R(13) independently of one another are hydrogen, —(C$_1$-C$_4$)-alkyl or benzyl;

and the other particular substituents R(2) and R(3) independently of one another are —(C$_1$-C$_4$)-alkyl, hydrogen, F or Cl;

R(4) and R(5) independently of one another are hydrogen, methyl, F, Cl, —OR(32), —NR(33)R(34) or —CF$_3$;

R(32), R(33) and R(34) independently of one another are hydrogen or methyl.

4. A process for the preparation of a compound of the formula I as claimed in claim 1, which comprises reacting a compound of the formula II

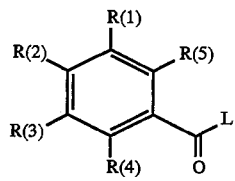

(II)

in which R(1) to R(5) have the meanings given in claim 1 and in which L is a leaving group which can easily be substituted nucleophilically, with guanidine.

5. A pharmaceutical composition for the treatment of arrhythmias, which comprises a compound of formula I as claimed in claim 1 together with a pharmaceutically acceptable carrier.

6. A pharmaceutical composition for the treatment of angina pectoris, which comprises a compound of formula I as claimed in claim 1 together with a pharmaceutically acceptable carrier.

7. A pharmaceutical composition for use in surgical operations and organ transplants, which comprises a compound of formula I as claimed in claim 1 together with a pharmaceutically acceptable carrier.

8. A pharmaceutical composition for the treatment of cardiac infarct, ischemic heart conditions, ischemic conditions of the peripheral and central nervous systems, of apoplexy, of peripheral organs and limbs, and of states of shock, which comprises a compound of formula I as claimed in claim 1 together with a pharmaceutically acceptable carrier.

9. A method for the treatment or prophylaxis of ischemic conditions of the heart, peripheral organs and limbs, the peripheral and central nervous system or of stroke, comprising administering an effective amount of a compound of the formula I as claimed in claim 1.

* * * * *

UNITED STATES PATENT AND TRADEMARK OFFICE
CERTIFICATE OF CORRECTION

PATENT NO. : 5,631,293
DATED : May 20, 1997
INVENTOR(S) : Heinz-Werner KLEEMANN et al.

It is certified that error appears in the above-identified patent and that said Letters Patent is hereby corrected as shown below:

Claim 1, column 16, line 3, "R(18)R(19)N—C=Y')" should read --R(18)R(19)N—(C=Y')--.

Signed and Sealed this

Twenty-first Day of July, 1998

Attest:

BRUCE LEHMAN

*Attesting Officer*   *Commissioner of Patents and Trademarks*